United States Patent [19]

Long

[11] 4,348,208

[45] Sep. 7, 1982

[54] URIC ACID ASSAY AND REAGENT SYSTEM THEREFOR

[75] Inventor: Robert L. Long, Indianapolis, Ind.

[73] Assignee: American Monitor Corporation, Indianapolis, Ind.

[21] Appl. No.: 315,165

[22] Filed: Oct. 26, 1981

[51] Int. Cl.³ ............................................. G01N 33/52
[52] U.S. Cl. .................................... 23/230 B; 23/925;
252/408; 422/61
[58] Field of Search ..................... 23/230 B, 905, 925;
252/408; 422/61

[56] References Cited

U.S. PATENT DOCUMENTS

| 3,528,777 | 9/1970 | Moran | 23/230 B |
| 3,536,448 | 10/1970 | Patel | 23/230 B |
| 3,649,198 | 3/1972 | Rush | 23/230 B |
| 3,801,466 | 4/1974 | Denney | 23/230 B X |
| 4,030,885 | 6/1977 | Das | 23/230 B |
| 4,201,694 | 5/1980 | Louderback | 23/230 B X |
| 4,288,343 | 9/1981 | Louderback | 23/905 X |

FOREIGN PATENT DOCUMENTS 54-33757  10/1979  Japan ...................................... 23/925

*Primary Examiner*—Arnold Turk
*Attorney, Agent, or Firm*—Robert A. Spray

[57] ABSTRACT

A diagnostic assay and reagent system for the determination of uric acid directly on a non-deproteinized sample of a biological fluid using an alkaline phosphotungstate reduction reaction in the presence of at least one organic sulfhydryl-containing compound.

18 Claims, No Drawings

URIC ACID ASSAY AND REAGENT SYSTEM THEREFOR

BACKGROUND OF THE INVENTION

1. Field of the Invention

This invention relates to a colorimetric method and reagent system for the determination of uric acid in biological fluids and more particularly to an improved phosphotungstate method preformed directly on serum and other fluids without deproteinization.

2. Nature and Significance of Accurate Uric Acid Assays

Medical science has long recognized that the measurement of uric acid in blood serum and other body fluids is a very useful and valuable tool in diagnosing and monitoring the course of a variety of pathological conditions. For example, when uric acid is present in abnormally high concentrations in the blood, it tends to crystallize out in the body joints, causing a very painful inflammatory condition known as gout. High uric acid blood levels are also known to be associated with such conditions as uremia and those characterized by an excessive destruction of the nuclei of white blood cells, e.g., leukemia and pneumonia.

In humans, uric acid is the waste product formed from the degradation of purines, which are principally derived from the ingestion of food. In healthy individuals, uric acid is filtered and removed from the blood by the kidneys and excreted in the urine. Determination of the amount or level of uric acid in the urine is thus quite important and useful in diagnosing and evaluating kidney diseases, for a variety of kidney diseases often affect the amount of uric acid excreted. Further, the amount of uric acid in urine provides an index of the amount of purines being metabolized, and thus the comparison of uric acid levels in blood serum and in the urine gives the physician valuable information which is useful in differentiating a variety of diseases affecting purine metabolism and kidney function.

Normal levels or quantities of uric acid in blood serum are very low, generally between only about 0.7 and 7.0 milligrams per 100 milliliters of serum. This very small amount or proportion of uric acid is emphasized by noting that its usual amount is only approximately one-tenth that of other body substances, such as glucose, which are measured for diagnostic purposes.

Accurate measurement of uric acid is demanding and difficult, since there are many substances in blood serum and urine which may be mistaken for uric acid in common assay methods; and if a mistakenly high value for uric acid is reported to the physician, the patient may be erroneously placed on potentially dangerous, expensive, uncomfortable, or unnecessary therapy. For example, if a patient has a high level of serum ascorbic acid, an erroneous and abnormally high uric acid value may be obtained by commonly used uric acid assay methods. This problem is compounded by the fact that even repeated assays to confirm the diagnosis will also produce erroneous results.

In addition to substances normally found in varying degrees in serum which may be mistakenly measured as uric acid, there are a number of substances either ingested in food or which are used as drugs which may interfere with accurate uric acid measurements. For example, caffeine from caffeine-containing beverages such as coffee, tea, and cola drinks, as well as gentisic acid, which is formed in the body from ingestion of aspirin, have been commonly and mistakenly measured as uric acid in prior art assay methods. Vitamin C when taken by the patient greatly elevates serum ascorbic acid levels, and this may also be mistakenly measured as uric acid.

3. Description of Prior Art and Attempts to Improve Specificity

The known methods for the determination of uric acid can be broadly classified into three categories: enzymatic methods utilizing the enzyme uricase, methods based upon the ability of uric acid to reduce alkaline phosphotungstate, and miscellaneous chemical colorimetric methods. The wide variety of methods currently in use today is testament to the fact that none of them is entirely satisfactory, and both past and present research in uric acid methodology has largely been directed toward improving specificity.

As long ago as 1894 (Offer, T. R., Centr. Physiol. 8, p. 801), it was reported that uric acid in an alkaline solution with phosphotungstic acid produces a blue color. Since that time, numerous alterations and modifications have been proposed for the determination of uric acid, all being based upon this ability of uric acid to reduce phosphotungstate. Such phosphotungstate reduction methods have been known and used for decades by thousands of scientists around the world. However, in spite of such longtime use and wide study, these methods still suffer from the fact that they lack specificity in the measurement of uric acid, since substances or chromogens other than uric acid which are found in serum or other body fluids, such as ergothionine, glutathione, ascorbic acid, glucose, creatinine, tyrosine, tryptophan, cystine, cysteine, caffeine, gentistic acid, and a variety of phenolic compounds, also react with alkaline phosphotungstate to give a blue color which may be falsely interpreted as originating from the uric acid chromogen.

Furthermore, in these phosphotungstate methods, protein precipitation and removal is necessary to prevent chromophore formation, and the consequent gross error, from the protein itself, and to prevent the formation of gross turbidity from the interaction of protein with subsequently used reagents. Such manipulation is not only cumbersome, expensive, time-consuming, and requires a large amount of sample, but it also reduces the accuracy of the uric acid assay itself. First, uric acid may be co-precipitated with protein, and thus its level in the sample may be underestimated. Moreover, where dialysis is used for removing protein, uric acid, being a large molecule with affinity for protein, may dialyze more slowly than interfering substances such as ascorbic acid, and thus the effect of the interference may actually be accentuated rather than diminished.

Thus, it can be seen that direct measurement of uric acid in serum without protein removal would be the most efficient and accurate method if interferences could be minimized without having to resort to such laborious and error-prone steps.

Even the phosphotungstate procedures of more recent years have been unable to provide the advantages of the present invention. A brief summary of such procedures helps to illustrate the advantageous significance of the present invention, and it further shows that the present invention is a departure from even phosphotungstate procedures. Moran, in U.S. Pat. No. 3,528,777 (Sept. 15, 1970) added an alkyl sulfate surfactant and hydrazine dihydrochloride in an attempt to eliminate protein interference in a direct phosphotungstate method for detection of uric acid. His method, however, required forty minutes reaction time and still did not provide for elimination of interference from sulfhydryl-containing compounds and other reducing substances in serum. Patel, in U.S. Pat. No. 3,536,448 (Oct. 27, 1970) also used a hydrazine compound, in combination with an amino carboxylic acid sequestering agent, in a phosphotungstate method. Patel's method also required a long reaction time (20 to 30 minutes) and recommended treatment of the sample to remove proteins. Rush, in U.S. Pat. No. 3,649,198 (May 19, 1970) used N-ethylmaleimide to pretreat serum prior to reaction with copper-neocuproine. Presumably, the N-ethylmaleimide reduced sulfhydryl interference, but the long reaction time, the requirement for a serum blank to help correct for other interferences, and the toxic nature of N-ethylmaleimide are serious limitations to this method. Denney, in U.S. Pat. No. 3,801,466 (Apr. 2, 1974) attempted to avoid protein removal and improve specificity for uric acid by treating a sample with uricase to destroy uric acid and then comparing the absorbance of a sample thus treated with the absorbance of an untreated sample following reaction of both samples with alkaline phosphotungstate. Although most common interferences were effectively eliminated by this method of subtracting them out, the problem of interference from endogenous sulfhydryls was not overcome. Furthermore, the procedure is time-consuming and utilizes an enzyme reagent which by nature is of limited stability.

SUMMARY OF THE INVENTION

It is a general object of the present invention to provide a novel colorimetric method for the assay of uric acid in biological fluids and a reagent system or compositions useful therefor. A more particular object of the present invention is to provide a direct method for uric acid assays without the need to remove protein from the sample. A further object is to provide such a method that is sensitive and requires only a very small amount of sample. Another object is to provide a method that is highly specific for uric acid. Yet a further object is to provide a method and reagent system which utilizes stable compositions of non-toxic substances. Still another object is to provide a method that is rapid and suited for use with current automated laboratory instrumentation. These and other objects, features and advantages will be apparent from the following description of the presently preferred embodiments of the present invention.

It was discovered that when certain sulfhydryl-containing compounds are included in a reaction mixture of an alkaline phosphotungstate reagent and a serum sample, the objects of the present invention are achieved.

The present invention involves the addition of an organic sulfhydryl-containing compound, preferably glutathione, and, optionally, a organic disulfide-containing compound, preferably 4,4-dithiodipyridine, to the reaction mixture of a serum sample and an alkaline phosphotungstate solution. A deep blue color develops almost instantly from the reduction of phosphotungstate by uric acid present in the sample. The method is so sensitive that an assay may be performed using a sample size of only 10 microliters or less.

The very beneficial but quite unexpected effect of including additional sulfhydryl-containing compounds is particularly surprising since sulfhydryl compounds normally found in biological fluids have been long known to produce undesired interferences in uric acid measurement. Indeed, many of the efforts of the prior art have been directed toward eliminating the errors resulting from the presence of a variety of sulfhydryl compounds found in biological samples. Thus, an achievement of the present invention is the avoidance of the interfering effect of endogenous sulfhydryls, not by any removal of such sulfhydryls, but by the surprisingly effective addition of even more sulfhydryls in a quantity substantially greater than that present in the samples themselves, in fact, in an amount such that the reaction system can be said to be overwhelmed by additional sulfhydryls.

For example, in the preferred embodiment described herein, the amount of glutathione used in the sulfhydryl reagent is 0.72 grams, or 720 milligrams per liter. As used in the assay of the embodiment, 0.5 milliliters of this sulfhydryl reagent is used in a final reaction volume totaling 3.5 milliliters. By calculation, one derives that the final concentration of the added glutathione is 0.36 milligrams, or 360 micrograms per 3.5 milliliters of reaction mixture. In contrast, the normal level of glutathione in whole blood is about 30 milligrams/100 milliliters (Ibbott, F. A., in Clinical Chemistry Principles and Technics, Henry, R. J. et al. editors, Harper and Row, Hagerstown, Md., 1974, p. 618). In the embodiment presented, 10 microliters of whole blood would thus be expected to contain about 0.003 milligrams, or 3 micrograms of glutathione. Therefore, the amount of additional glutathione in the reaction mixture is about 120 times the amount endogenously present in the whole blood sample, thus overwhelming the reaction with an additional sulfhydryl-containing compound.

More particularly, according to the novel concepts of the present invention, quite in contrast to the known deleterious effect of endogenous sulfhydryl compounds, exogenous sulfhydryl-containing compounds used in the present invention seem to activate, accelerate or otherwise accentuate the reaction of uric acid with alkaline phosphotungstate in what seems to be a selective fashion relative to common interfering substances such as ascorbic acid, protein and other reducing substances normally found in blood serum. Consequently, uric acid can be measured very specifically relative to such commonly interfering substances.

In performing diagnostic assays, it is customary and convenient for laboratory and other analytical personnel to use pre-formulated reagent compositions which are available on a commercial basis from various manufacturers and generally known as kits. A diagnostic kit is comprised of the one or more pre-formulated reagents that make up the reagent system used to perform the assay, and the kit may also contain appropriate calibration and quality control materials. For economic considerations, the kit may also be in the form of the one or more pre-formulated reagents packaged individually or in bulk form for a specific intended use.

With respect to the present invention, it is desirable that the uric acid kit comprise several separate, preformulated reagents for enabling maximum shelf stability of the components while minimizing further reagent preparation steps for the analyst. These kit reagents are a phosphotungstic acid reagent, an alkalinizing reagent, a concentrated or stock sulfhydryl reagent, and, optionally, a diluent for the sulfhydryl reagent. In the preferred embodiment presented, the alkalinizing reagent is a cyanide-free carbonate reagent, but it is not beyond the scope of the present invention to use other types of alkalinizing reagents compatible with phosphotungstate methods and generally known to those skilled in the art. The diluent for the sulfhydryl reagent desirably contains one or more stabilizing, antimicrobial, or preservative ingredients for prolonging the stability of the sulfhydryl reagent in its diluted form as used in performing the assay.

DESCRIPTION OF THE PREFERRED EMBODIMENTS

The specific embodiments of the present invention detailed herein are provided to enable an analyst skilled in the art to understand and produce reagents and to perform an assay according to the novel concepts and achievements of the present invention.

EXAMPLE 1

Reagent Preparation

A phosphotungstic acid reagent is prepared by making a first solution consisting of 26.6 grams molybdate-free sodium tungstate and 21.2 grams 85% phosphoric acid brought to a volume of 1 liter with deionized water. After refluxing this solution, with vapor recovery, for two hours, 6 microliters bromine are added. Finally, 21.2 grams lithium sulfate are brought to a volume of 1 liter using the first solution.

An alkalinizing carbonate reagent is prepared by combining 100 grams anhydrous sodium carbonate, 200 grams urea, 5 grams tetrasodium EDTA, 5 milliliters Neodol® 25-3S, 500 milligrams sodium lauryl sulfate and sufficient deionized water to give a final volume of 1 liter. (Neodol is the registered trademark for Shell Chemical's detergent alcohols. Neodol 25-3S is an ethoxysulfate surfactant and commercially available.)

A sulfhydryl reagent is prepared by adding 0.72 grams reduced glutathione, 3.2 milligrams 4,4-dithiodipyridine, and 1 milliliter concentrated hydrochloric acid to sufficient deionized water to give a final volume of 1 liter.

In an alternative embodiment, this sulfhydryl reagent may be made up in a concentrated form, dispensed into small vials and lyophilized or freeze-dried. This method of preparation is especially desirable when manufacturing diagnostic kits wherein maximum stability of the preformulated reagents is especially important. Prior to performing an assay, the analyst merely reconstitutes the dried sulfhydryl reagent with deionized water or a preformulated diluent which may contain antimicrobial or preservative agents.

EXAMPLE 2

Determination of Uric Acid

To perform an assay for uric acid, the following are combined in a test tube or reaction vessel: 1.5 ml of the carbonate reagent, 0.5 ml of the sulfhydryl reagent, 10 ul of the sample to be assayed, and 1.5 ml of the phosphotungstate reagent. Preferably, the reaction is carried out at 37° C. and the absorbance measured at a wavelength of about 760 nm. Due to the gradual increase in absorbance that occurs when the reagents themselves are combined in the absence of a uric-containing sample (i.e., a blank reaction), it is important that substantially identical timed intervals be used for each sample and calibration material assayed. By using such timed intervals from the time of the addition of the phosphotungstate reagent to the time of the measurement of the absorbance, the contribution of the blank absorbance to the total absorbance reading will be substantially the same for all specimens so assayed.

Calculation of the amount of uric acid in the sample assayed is determined by dividing the absorbance reading of the unknown sample by the absorbance reading of the calibrator or standard, and then multiplying the result thus obtained by the uric acid concentration of the calibrator or standard.

The absorbance is preferably measured 90 seconds following the addition of the phosphotungstate reagent to the reaction mixture; however, the timed intervals used may be any between about 1 minute and 30 minutes, as long as the interval selected is precisely and exactly used for all samples and calibration materials assayed.

Due to the nature of the timing requirements of the reaction, the present invention is advantageously practiced using laboratory instrumentation (i.e., analyzers) capable of automatically sampling specimens, dispensing reagents, and measuring absorbance with precise exactness of timing. An example of such an instrument is the KDA ® analyzer manufactured by American Monitor Corporation, Indianapolis, Ind., which has been used in carrying out a preferred embodiment of the present invention. Other suitable analyzers are many of those as currently in use in clinical laboratories, such as the AutoAnalyzer TM manufactured by Technicon Instruments Corporation, Tarrytown, N.Y.; the Poli-Mak TM analyzer manufactured by PM America; the ABA-100 TM bichromatic analyzer manufactured by Abbott Laboratories, Inc.; and the Parallel TM analyzer manufactured by American Monitor Corporation.

The sulfhydryl reagent preferably includes at least two sulfhydryl compounds. The glutathione used in the preferred embodiment of the present invention is a reduced organic sulfhydryl, and the reagent in which it is contained should be acidic in nature in order that it remain in a reduced form. This organic sulfhydryl is responsible for the greatly increased sensitivity and specificity of the present invention over current phosphotungstate methods. The 4,4-dithiodipyridine included in the preferred embodiment is an oxidized sulfhydryl, or disulfide. Its inclusion is for the purpose of extending the linear range of the assay, i.e., the range over which accurate and useful results may be obtained. It is also thought to help stabilize the reduced sulfhydryl compound.

In the alternative embodiment described, the sulfhydryl reagent is prepared as a concentrated, dried reagent and, optionally, a diluent preservative reagent which are mixed together prior to performing the assay. This is done to reduce preparation time and expense and to improve the stability of the reagents. Manufacturers of diagnostic reagent kits desirably configure the components of such kits to provide for maximum shelf stability of the components. The individual laboratory worker practicing the present invention, however, may prefer to prepare the sulfhydryl reagent directly in its final form and ingredient concentration as used in the assay. In the embodiment presented, the sulfhydryl reagent, in the form in which used in the assay, remains stable for approximately a month under refrigeration and in the absence of bacterial contamination.

The preferred sample to reagent volume ratio presented (1:350) may also be varied as much as 40% without departing from the novel concepts of the present invention. Examples of suitable biological specimens are serum, plasma, urine, synovial fluid, and cerebrospinal fluid. For best performance of the assay when practicing the invention using serum specimens and the reagent compositions of the embodiment presented, the preferred sample to reagent volume ratio should not be greater than 1:350 but may be as low as 1:500 without loss of utility. The ratio selected will normally be one that is compatible with the capabilities of the particular instrumentation employed in practicing the invention. The use of ratios as high as 1:200 will result in a loss in linearity of the assay, whereas a loss in sensitivity will be seen when using ratios less than 1:600.

The type and number of sulfhydryl compounds selected to practice the invention do not need to be limited to those presented here as a preferred embodiment; however, at least one sulfhydryl-containing compound must be used, preferably organic in nature and in its reduced form. In addition to glutathione, other useful organic sulfhydryl compounds include N-acetylcysteine, 1,4-dithiothreitol, dithioerythritol, cysteine, mercapto-ethanol, and mercaptopropanol.

Photometric measurement of the colored reaction product may be made at any suitable wavelength between 600 and 800 nm, and, where instrumentation is used employing bichromatic measurements, two appropriate wavelengths may be utilized. Further, it is not considered to be beyond the scope of the present invention to make photometric measurements using reflectance techniques rather than absorbance techniques.

Other modifications and alterations to the foregoing embodiments will be apparent to those skilled in the art and are not to be considered beyond the scope of the novel concepts of the present invention.

What is claimed is:

1. In a method for the determination of uric acid in a fluid sample wherein said sample is reacted with phosphotungstate under alkaline conditions, the improvement comprising the step of accelerating the reaction between uric acid and phosphotungstate by including in the reaction mixture thereof at least one sulfhydryl-containing compound in an amount substantially greater than that endogenously present in said sample, thereby increasing the sensitivity and specificity of the reaction for uric acid.

2. A method as recited in claim 1, wherein said sulfhydryl compound is an organic sulfhydryl-containing compound.

3. A method as recited in claim 2, wherein said sulfhydryl compound is selected from the group consisting of glutathione, N-acetylcysteine, 1,4-dithiothreitol, dithioerythritol, cysteine, mercaptoethanol, and mercaptopropanol.

4. A method as recited in claim 2, wherein said sulfhydryl compound is glutathione.

5. A method as recited in claim 2, 3, or 4, further comprising the step of enhancing the linearity of the reaction by including an organic disulfide compound.

6. A method as recited in claim 5, wherein said disulfide compound is 4,4-dithiodipyridine.

7. In a reagent composition for the determination of uric acid in a fluid sample with alkaline phosphotungstate, the improvement wherein said composition comprises at least one sulfhydryl-containing compound in a quantity substantially greater than that endogenously present in said sample to increase the sensitivity and specificity of the composition for uric acid.

8. A composition as recited in claim 7, wherein said sulfhydryl compound is an organic sulfhydryl-containing compound.

9. A composition as recited in claim 8, wherein said sulfhydryl compound is selected from the group consisting of glutathione, N-acetylcysteine, 1,4-dithiothreitol, dithioerythritol, cysteine, mercaptoethanol, and mercaptopropanol.

10. A composition as recited in claim 8, wherein said sulfhydryl compound is glutathione.

11. A composition as recited in claim 8, 9, or 10, further comprising an organic disulfide compound.

12. A composition as recited in claim 11, wherein said disulfide compound is 4,4-dithiodipyridine.

13. A diagnostic kit for the determination of uric acid in a biological sample, comprising a phosphotungstic acid reagent, an alkalinizing reagent, and a sulfhydryl reagent comprised of at least one sulfhydryl-containing compound.

14. A kit as recited in claim 13, wherein said sulfhydryl compound is an organic sulfhydryl-containing compound.

15. A kit as recited in claim 14, wherein said sulfhydryl compound is selected from the group consisting of glutathione, N-acetylcysteine, 1,4-dithiothreitol, dithioerythritol, cysteine, mercaptoethanol, and mercaptopropanol.

16. A kit as recited in claim 14, wherein said sulfhydryl compound is glutathione.

17. A kit as recited in claim 14, 15, or 16, wherein said sulfhydryl reagent further comprises an organic disulfide compound.

18. A kit as recited in claim 17, wherein said disulfide compound is 4,4-dithiodipyridine.

* * * * *

UNITED STATES PATENT AND TRADEMARK OFFICE
CERTIFICATE OF CORRECTION

PATENT NO. : 4,348,208
DATED : September 7, 1982
INVENTOR(S) : Robert L. Long

It is certified that error appears in the above—identified patent and that said Letters Patent is hereby corrected as shown below:

Col. 2, line 33: The word "gentistic" should be: --gentisic--.

Col. 3, line 58: The word "a" should be: --an--.

Col. 5, line 62: Change the phrase "uric-containing" to: --uric acid-containing--.

Signed and Sealed this

Fourth Day of January 1983

[SEAL]

Attest:

GERALD J. MOSSINGHOFF

Attesting Officer

Commissioner of Patents and Trademarks